United States Patent [19]

Leonard et al.

[11] Patent Number: 4,928,313
[45] Date of Patent: May 22, 1990

[54] METHOD AND SYSTEM FOR AUTOMATICALLY VISUALLY INSPECTING AN ARTICLE

[75] Inventors: Patrick F. Leonard; Donald J. Svetkoff; Robert W. Kelley; Donald K. Rohrer, all of Ann Arbor; E. North Coleman, Jr., Dearborn Heights, all of Mich.

[73] Assignee: Synthetic Vision Systems, Inc., Ann Arbor, Mich.

[21] Appl. No.: 355,816

[22] Filed: May 19, 1989

Related U.S. Application Data

[63] Continuation of Ser. No. 140,667, Jan. 4, 1988, abandoned, which is a continuation of Ser. No. 791,470, Oct. 25, 1985, abandoned.

[51] Int. Cl.⁵ .............................................. G06K 9/00
[52] U.S. Cl. ............................................ 382/8; 382/49; 358/101
[58] Field of Search ............... 382/8, 49, 86; 358/101, 358/106, 107

[56] References Cited

U.S. PATENT DOCUMENTS

| | | | |
|---|---|---|---|
| 4,148,065 | 4/1979 | Nakagawa et al. | 382/8 |
| 4,242,662 | 12/1980 | Tsujiyama et al. | 382/8 |
| 4,310,827 | 1/1982 | Asai | 382/55 |
| 4,399,554 | 8/1983 | Perkins et al. | 382/55 |
| 4,473,842 | 9/1984 | Suzuki et al. | 358/107 |
| 4,477,926 | 10/1984 | Linger et al. | 382/8 |
| 4,481,664 | 11/1984 | Linger et al. | 382/8 |
| 4,510,616 | 4/1985 | Lougheed et al. | 382/8 |
| 4,520,505 | 5/1985 | Yamamoto et al. | 382/55 |
| 4,570,180 | 2/1986 | Baier et al. | 358/106 |
| 4,589,140 | 5/1986 | Bishop et al. | 382/8 |
| 4,602,333 | 7/1986 | Komori | 382/56 |
| 4,650,333 | 3/1987 | Crabb et al. | 358/106 |
| 4,692,943 | 9/1987 | Pietzsch et al. | 382/8 |

*Primary Examiner*—Leo H. Boudreau
*Assistant Examiner*—Jose L. Couso
*Attorney, Agent, or Firm*—Brooks & Kushman

[57] ABSTRACT

A method and system are disclosed for automatically visually inspecting an article such as an electronic circuit wherein both reference and non-reference algorithms are utilized to detect circuit defects. The system includes a pipelined cellular image processor which is utilized to implement the non-reference algorithm and an arithmetic logic unit (ALU) is coupled to the output of the cellular image processor to perform the reference method. The non-reference method includes a spaces and traces algorithm and the reference method includes a topology matching algorithm. The system also includes an algorithm for locating and gauging critical areas of the circuit with sub-pixel accuracy. The cellular image processor is supported by a matched host image processor system

14 Claims, 5 Drawing Sheets

TOPOLOGY CHECK

Fig. 9

PATH AND SPACE CHECKING

Fig. 10

METHOD AND SYSTEM FOR AUTOMATICALLY VISUALLY INSPECTING AN ARTICLE

This is a continuation of co-pending application Ser. No. 140,667 filed on Jan. 4, 1988 now abandoned which is a continuation of Ser. No. 791,470 filed Oct. 25, 1985, now abandoned.

TECHNICAL FIELD

This invention relates to a method and system for automatically visually inspecting articles and, in particular, to methods and systems for automatically visually inspecting articles such as electronic circuits.

BACKGROUND ART

The electronic revolution of the 80's has brought about further miniaturization of electronic devices and circuits and with it an ever-increasing need for automatic visual inspection. As product reliability becomes increasingly more important, electrical testing alone is not sufficient to detect many of the defects affecting long-term reliability. Thus visual inspection is required. This is a difficult task for human inspectors due to the vast amounts of information that must be processed at ever-increasing production rates within strict resolution requirements.

Virtually all phases of automatic visual inspection of electronic circuits is the subject of current research. Researchers have analyzed circuit flaws and specified some algorithms for detecting them. Other researchers have described prototype printed wiring board (PWB) inspection systems and imaging and image processing of thick film circuits. Computer vision technology has also being proposed for inspecting integrated circuits (IC's).

Much of the research currently being done is also applicable to the general problem of inspecting two-dimensional patterns having several colors and shades of gray. This includes character recognition, inspecting for defects in discs and tapes, CRT inspection, etc.

The need for high-performance image analysis systems in industrial, scientific and defense applications has speeded the development of high-speed image processor architectures. One of the most promising techniques for the construction of fast, efficient vision systems centers on the concept of cellular automata.

Early investigators in the field of image processing identified the unique capability of cellular computer architecture to solve vision problems. However, while these designs had potential for good performance in machine vision applications, system performance was limited by the circuit technology available to build such machines. Advances in integrated circuit technology have made cellular processors practical for incorporation into machine vision systems.

Machine vision image operations generally require substantial amounts of low-level, computationally intense, point and neighborhood computations. Tasks such as electronics inspection require the analysis of tremendous amounts of data from which spatial integrity of circuit patterns is inferred. Local neighborhood operations are ideal for this purpose. By contrast, medical data processing typically operates on images with low signal-to-noise levels and substantial signal enhancement through filtering is necessary.

Key requirements of a machine vision system are reprogrammability and good future growth capability to accommodate changes in the environment of the system after the system is installed.

One type of cellular processor particularly adaptable for machine vision applications is called the Cytocomputer. The Cytocomputer includes a series of pipelined processor stages. Pipelining is a form of processor parallelism commonly termed "temporal parallelism". Each processor stage of the Cytocomputer comprises an eight-bit, general purpose, neighborhood image processor. Each stage executes a logical, comparison or arithmetic function on a three-by-three neighborhood of pixels and transmits the result to its succeeding stage in the pipeline. A characteristic example of such a function is a Sobel operator or a maximum neighbor selection. Images to be transformed are serially input to the Cytocomputer in a raster scan format, with the effect that a three-by-three window "slides" across the image in a raster scan fashion.

The Cytocomputer is capable of executing a range of image processing tasks at high speed due to its relatively efficient architecture. Organization of the stage processing elements as a systolic array allows multiple use of each input data item thereby reducing the system's communication costs and complexity. The systolic approach also provides a simple, regular, internal stage architecture that allows the image to flow through the stage at the maximum rates afforded by the technology of the integrated circuit.

Each Cytocomputer processing element is based on a custom gate array which contains about 2,500 equivalent gates. Consequently, each processing element can execute neighborhood operations at a rate exceeding 10 million pixels per second.

Each processor stage is organized as a three-by-three systolic array of neighborhood pixel processing elements. A set of delay line memories is used to form the neighborhood window and data from the window flows through the array of processing elements. The output signals from the nine processing elements are combined according to specified Cytocomputer instructions so that a replacement pixel value is generated and passed to the next stage in the pipeline. The Cytocomputer is fully pipelined internally so that after a delay to fill the pipeline, a processed pixel is output from the stage whenever an input pixel is clocked into the stage.

The ability to pipeline stages is a key feature which results in high performance of the Cytocomputer. Each stage is capable of processing 10 million pixels per second and a pipeline of 10 such stages is capable of 100 million eight-bit pixel operations per second. In a typical application a 10-stage pipeline can perform any 10 point or neighborhood instructions on a 512×512 pixel image in less than one video frame time (i.e. 33 milliseconds). For example, the Sobel operator can be performed on a 512×512 image in 26.2 milliseconds. In principle large numbers of stages can be pipelined. However, in practice, most applications are satisfied by Cytocomputers on the order of eight to 10 stages long since non-Cytocomputer devices contained within the system soon become bottlenecks to system performance.

The basic neighborhood processing technique is essential to most important low and medium-level image transformation and the Cytocomputer is optimized to perform these operations. The Cytocomputer was originally designed for morphological operations such as erosions, dilations and skeletonizations. Mathematical morphology is a compact method of performing gauging operations in machine vision tasks. For example, inspection of a thick film substrate or an integrated circuit mask for design rule violations can be performed as a series of erosions and dilations as illustrated in U.S. Pat. No. 4,441,207. An image of such a circuit can be globally inspected for short and open circuits in a few time frames.

The Cytocomputer also supports most common linear mask operations such as Sobel, Roberts, Laplacian and gradient and also common 3×3 convolutions. These operations are pipelined and can be performed along with morphological operations.

Further details of the Cytocomputer can be obtained from the U.S. Patents assigned to the Environmental Research Institute of Michigan, all of which are hereby incorporated by reference.

Several types of algorithms or methods for detection of electronic circuit defects have been developed over the years. These algorithms and the systems utilizing same can be classified into three general categories: reference system pattern matching; non-reference or generic property verification; and, measurement or gauging.

Reference systems compare pixel values or properties of a known good circuit with those of a circuit under test. The matching may be done by direct comparison of intensity values, by comparison of statistical or spatial features, or by matching nodes and end points in a graph which defines the topology of the circuit. Mismatches between the reference pattern and the image under test are used to detect flaws. One advantage of the reference approach is that much of the knowledge required to determine if a circuit is good is contained within the reference pattern. One of the problems with this approach is the difficulty in accurately registering or aligning the two images for comparison, thereby resulting in an ambiguity range between a good and a defective circuit. Another problem with the reference approach is that the data representation of the reference image must be sufficiently compact to avoid excessive memory costs and slow data transfer rates. In general, the reference method is good in finding gross defects but has more trouble in detecting flaws small in size relative to the entire image because of the misregistration problem.

Non-reference systems differs from reference systems in that no comparison between the image to be inspected and a reference image is needed. This approach does not average the various features in an image into a single statistic or set of statistics but instead analyzes each of the features individually. Thus an important advantage of this approach is that no information is lost. Such a system searches an image for the presence of a specific set of features. Flaws are detected by the presence or absence of these features. In order for such a system to be successfully implemented, the set of guidelines used to detect or describe any given feature must be unambiguously defined and must be applicable throughout the entire image being inspected.

The non-reference method is most effective in applications where a set of rules applies to each point in the circuit. If this method is to be exclusively used, then the inspection criteria must be described by a compact, context-independent set of specifications. Unfortunately, design rules are routinely violated throughout the circuit manufacturing industry without affecting the functionality of a circuit design such as a thick film circuit design. With respect to thick film designs, the presence of multiple layers can cause the appearance of violations when in fact no error has occurred. The impact on the non-reference method is that the list of inspection rules can potentially become very long, resulting in a time-consuming algorithm. In summation, the non-reference method is not general enough to be applicable under a wide variety of conditions and often becomes "crippled" when rule violations occur.

Measurement or gauging systems are often designed to report dimensions of patterns and provide feedback (X, Y and theta measurements for alignment) for process control. These systems assume that the measurement area is defect free and that a good estimate, at least in a least squares sense, is available to locate the position of each pattern precisely. Most commercially available circuit board inspection systems do not provide full-function circuit inspection and dimensional measurement. For hybrid inspection systems alignment is very important and in integrated circuit inspection systems precise line width measurements are required. Measurement accuracy at any single location is also affected by digitization. Confidence in the measurement is typically plus or minus the size of each pixel or picture element.

Thick film electronic circuits are commonly produced on a ceramic substrate. Several layers consisting of a conductor, resistor, dielectric and solder paste patterns are printed with various inks onto the substrate using screen printing and subsequent firing processes. After these operations, components are placed onto the substrate. Automatic visual inspection of each of the printed layers before component assembly is desired since checking such circuits is putting ever more strain on human inspectors. Designs are growing more complex with thinner lines, larger substrates and the greater user of multilayer construction. This inspection must be performed both before and after firing the individual layers (i.e. when both the layer is wet and again when it is dry). Typical flaws include voids, cracks, misalignment, path spacing and width errors etc. Resolution required from inspection is typically in excess of one mil (i.e. 0.001 inch). The surface area of each circuit is frequently one million square mils.

Missed defects because of lapses in human concentration or fatigue can be expensive. Buried flaws in multilayer circuits are virtually impossible to repair. The cost of a defect multiplies if it reaches the next stage of production which is assembly.

Inspection time becomes more and more an issue as manufacturers move into large substrates of dense, multilayer designs. In such cases, human inspection of the layers may be measured in minutes. The task puts a heavy burden on manufacturing people creating a potential bottleneck. It is desirable if such automatic vision systems be capable of generating a data base necessary for statistical reporting to achieve process control.

DISCLOSURE OF THE INVENTION

An object of the present invention is to provide an improved method and system for automatically visually inspecting an article which combines both reference and non-reference algorithms to provide rapid and reliable inspection.

Another object of the present invention is to provide a method and system for automatically visually inspecting an electronic circuit using both reference and non-reference algorithms and which also has the capability of locating and gauging critical areas in the circuit pattern with sub-pixel accuracy.

Yet still another object of the present invention is to provide a system for automatically visually inspecting an article including a cellular image processor to perform neighborhood operations and an arithmetic logic unit to perform image and scalar operations for rapid and cost-effective inspection.

In carrying out the above objects and other objects of the present invention a method for automatically visually inspecting articles comprises the steps of acquiring a first set of image data representing a known article and acquiring a second set of image data representing an article under inspection. The method further comprises the step of processing both sets of image data to separate each of the images into at least two identifiable areas having a boundary therebetween. The method also includes the step of checking the second set of processed image data with at least one preselected geometrical constraint to identify areas in noncompliance. Also, the two sets of processed image data are matched to identify areas where mismatches occur.

A system for automatically visually inspecting an article comprises means for acquiring first and second sets of image data wherein the first set of image data represents a known good article and the second set of image data represents an article under inspection. The system also comprises means for processing both sets of image data to separate each of the images into at least two identifiable areas having a boundary therebetween. The system includes means for checking the second set of processed image data with at least one preselected geometrical constraint to identify areas of non-compliance. Means are also provided for matching the two sets of processed image data to identify areas where mismatches occur.

The advantages of the above method and system are numerous. For example, flaws are detected in a rapid and reliable fashion due to the combined approach of matching a segmented image with an image-like representation of a defect free article and by using a minimum width/spacing violation detector. In this way the limitations of both the reference and non-reference algorithms are substantially overcome.

Furthermore, the method and system combine the best elements of design matching, design rule checking and measurement to thereby obtain high throughput and high accuracy while still remaining cost effective. This method and system are sufficiently general and applicable to the inspection of different types of circuits such as PWB's and IC's and also to the general problem of inspecting two dimensional patterns which have several colors and shades of gray. This includes character recognition, inspecting for defects in disks and tape, CRT inspection, etc.

Other advantages of the present invention will be readily appreciated as the same becomes better understood by reference to the following detailed description when considered in connection with the accompanying drawings.

BEST MODE FOR CARRYING OUT THE INVENTION

Figure 1:
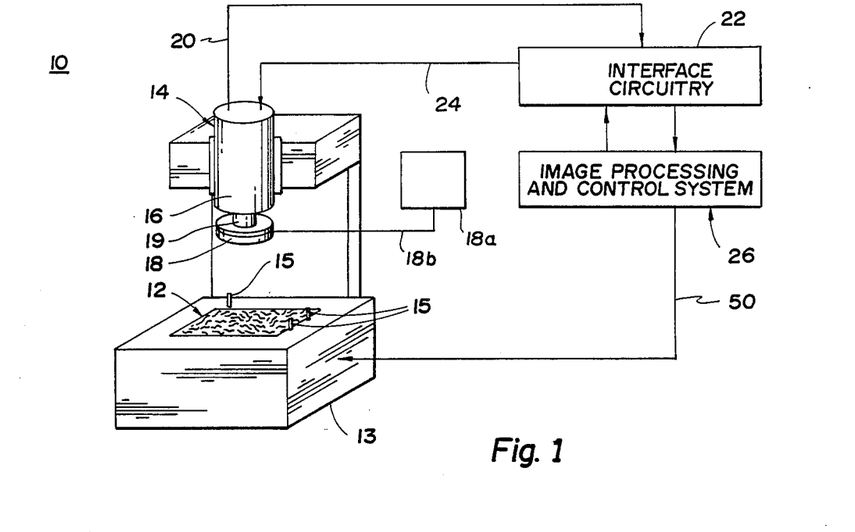
FIG. 1 is a schematic view of an automatic visual inspection system constructed in accordance with and operable for practicing the method of the present invention.
Figure 2:
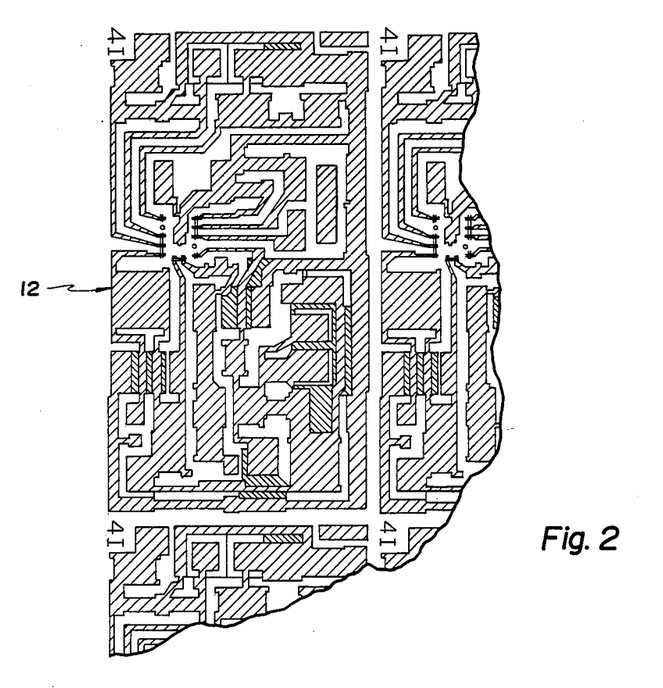
FIG. 2 is a top plan view, partially broken away, of a thick film circuit capable of being inspected in accordance with the method and system of the present invention.

Referring now to FIG. 1 of the drawings there is illustrated a system, collectively indicated at 10, for automatically visually inspecting an article. As illustrated herein, the article may comprise thick film electronic circuits, generally indicated at 12, produced on a ceramic substrate as shown in FIG. 2.

Figures 3, 4:
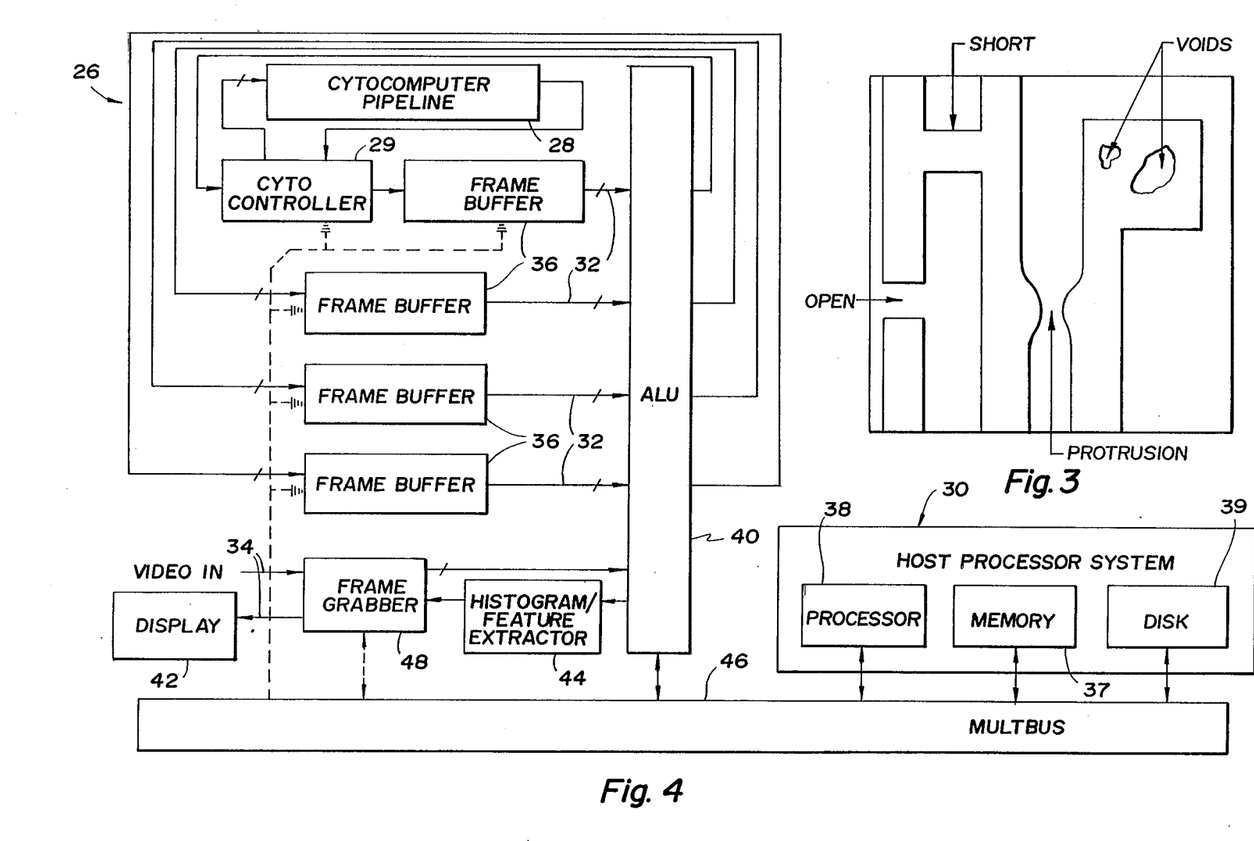
FIG. 3 is aschematic top plan view of a portion of the circuit of FIG. 2 illustrating various circuit defects.
FIG. 4 is a schematic block diagram of the electronic hardware used in the system.

The system 10 is able to identify certain materials and detect defects such as shorts, opens, voids, extra material and misregistration of the layers of the film circuit 12. Examples of such defects are shown in FIG. 3.

While the article under inspection described hereinafter comprises a substrate of thick film electronic circuits 12, it is to be understood that other types of electronic circuits such as PWB's and IC's may also be inspected by the method and system described herein. Also, two-dimensional patterns having several colors and shades of gray may also be inspected by this method and system.

The system 10 includes an illumination and imaging subsystem, generally indicated at 14, for providing a high contrast image of the circuit 12 being tested. As illustrated in FIG. 2, to the human observer the materials which make up the thick film circuit 12 may appear in varying colors and shades of gray and may be wet, dry or fired at various stages of production. Thick film conduction materials include silver palladium, silver, gold, and copper, all of which differ in appearance. Wet resistors are often very dark and have a strong specular reflection component when wet. Dielectrics are often transparent and therefore color is often added for visual identification. It is not uncommon to find several color-coded dielectrics and different conductor types printed on a single substrate. For example, a multilayer circuit board may have gold and silver palladium conductors, blue and green dielectric patterns and resistors.

Polarization and color discrimination techniques are useful for acquiring a high contrast image of the circuit 12 under a wide variety of conditions. Color information can also be used to aid subsequent segmentation of the image for which a monochrome image is not sufficient for discrimination of the materials. Separation between dielectric and substrate in a monochrome image is possible by using different narrow band filters which can be selected to maximize the difference in spectral response between the dielectric and substrate.

While not specifically utilized in the method and system of the present invention, multichannel and color imaging may be utilized for more complex multilayer hybrid circuits.

As illustrated in FIG. 2, the minimum line widths and spacings between different circuit materials range from about 10 mils down to about 2 mils. Preferably, digitization of the analog image signal is done at approximately 1/10th of the minimum design rule utilized as described in more greater detail hereinafter. Resolution and depth of field requirements for imaging such a circuit shows that 0.2 mils is the approximate practical resolution limit without using an autofocus camera.

The subsystem 14 includes a F/8 microscope zoom-objective camera 16 for imaging the circuit 12 over the needed magnification range. The camera 16 preferably comprises a solid state CCD array camera. A halogen lamp 18a is connected to a ring illuminator 18 via a fiber-optic bundle 18b for illuminating the article under inspection.

The output of the camera 16 appears on a line 20 and comprises a digitized signal representing the optical power received. A camera status signal is also provided along the line 20 and is input to interface circuitry 22. The interface circuitry 22 outputs control signals along line 24 to the camera 16 to control its operation and interfaces with an image processing and control system generally indicated at 26 in FIGS. 1 and 4.

The circuit 12 is supported on a fixture 13 having solenoids (not shown) contained therein to control locating pins 15 which, in turn, position the circuit 12 on the fixture 13. The camera 16 is supported on a camera stand or support structure adjacent the fixture 13.

Referring again to FIG. 4, there is illustrated in detail the architecture of the system 26. The system 26 includes a Cytocomputer pipeline 28 controlled by a Cyto controller 29 as previously described herein, in U.S. patent application entitled "Image Analyzer System Having Neighborhood Arithmetic Processing Capabilities", and in the references cited therein. The controller 29 interfaces the bus architecture of the host system to that of the pipeline 28 and provides local storage of Cytocomputer programs.

The pipeline 28 is supported by a host system including a host processor system, generally indicated at 30. Control provided by the host processor system 30 is provided by a processor 38 which preferably comprises an MC 68000 processor of the Motorola Corporation. The system 30 also includes a local memory 37 supported by an appropriate peripheral such as a hard disc 39. The host processor system 30 communicates with the remainder of the system 26 by means of a Multibus 46 from the Intel Corporation.

In general, the components of the host system are chosen to operate at a speed adequate to efficiently use the pipeline 28. The pipeline 28 is preferably supported by an image processor called the IP-512, from Imaging Technology, Inc. of Woburn, Mass. The host system comprises four video rate, (i.e. 10 MHz) eight-bit data busses 32 for image transfers and two analog video rate busses 34 for image acquisition and display.

The host system also includes four high-speed image memories or frame buffers 36 coupled to the pipeline 28 and the system 30 to provide transparent dual port access for both the processor 38 and video bus I/O. Each buffer 36 contains independent pan and scroll control, as well as pixel and memory plane protection. Images may be acquired into any of the buffers 36.

The host system also includes a 16-bit software controlled ALU board or ALU 40 coupled to each of the buffers 36 and the system 30. Preferably, the board 40 comprises the ALU-512 of Imaging Technology, Inc.

The output of the pipeline 28 is directed by the controller 29 through one of the frame buffers 32 to the ALU 40 which combines stored images from the host processor system 30 with the pipeline processed results. This capability is useful when neighborhood processing is performed on an acquired image and the results are compared against a template image by the ALU 40 as will be described in greater detail hereinbelow.

The ALU 40 also acts as a central switching device for the data busses 32. Furthermore, the ALU 40 performs arithmetic and logical functions and contains a 16-bit barrel shifter and an eight-bit multiplier. The ALU 40 also controls the acquisition and display of images on a display 42.

The host system also includes a histogram/feature extractor 44, which preferably comprises an HF-512 also available from Imaging Technology, Inc. The histogram/feature extractor 44 extracts up to 4,096 features in one frame time and computes a histogram in two frame times based thereon. The results of the process are available to the host processor system 30 via the multibus 46.

The host system further includes an analog processor or a frame grabber/display controller 48 which preferably comprises an AP-512 from Imaging Technology, Inc. The processor 48 is coupled to the display 42, the extractor 44 and the ALU 40. The processor 48 is capable of supporting two video cameras and has three output channels for pseudocolor operation, as well as three composite video outputs.

The combination of the pipeline 28 and the ability of the ALU 40 to control data bus interconnections allows multiple images to be simultaneously switched between frame buffers 36 and sent to the various processing elements such as the pipeline 28, the ALU 40, the histogram/feature extractor 44, and the video display 42 by appropriate programming of the data path interconnections. This allows multiple system operations to occur in parallel with operations within the pipeline 28. Furthermore, in addition to processor parallelism in the pipeline 28, images may be manipulated in parallel at the system level.

Figure 5:
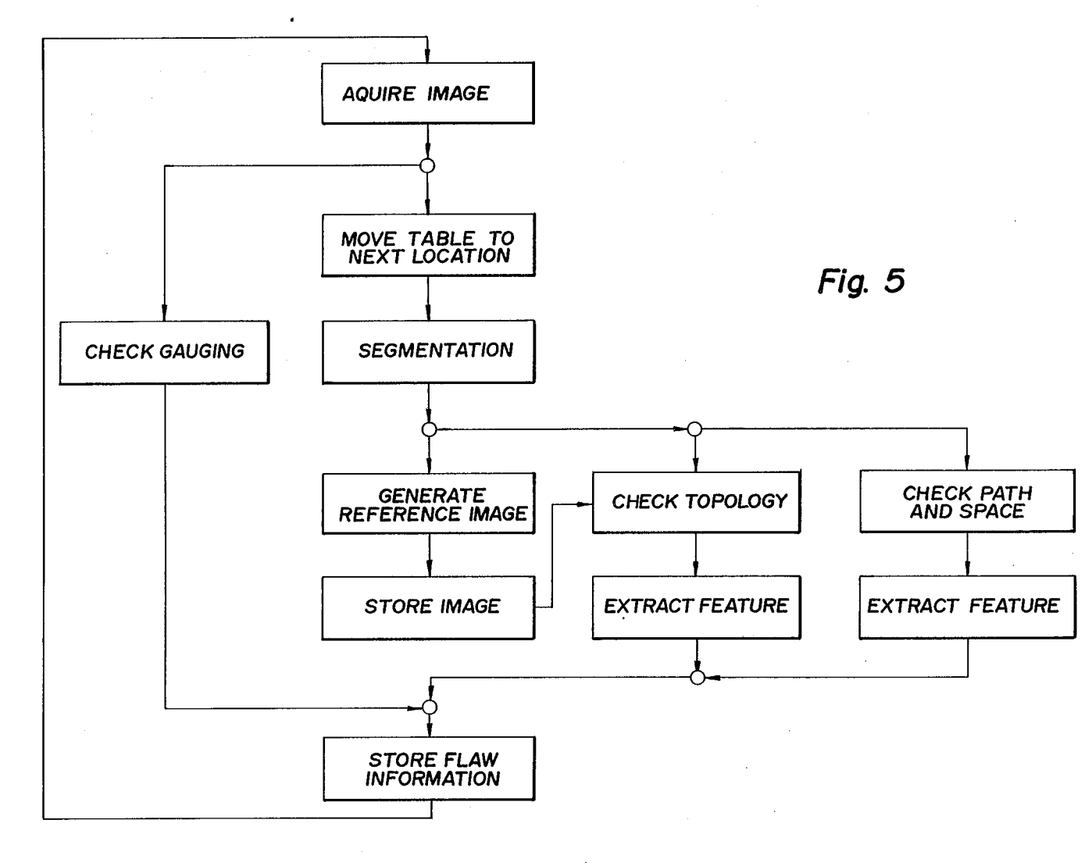
FIG. 5 is a generalized block diagram of the method of the present invention.

Referring now to FIG. 5, there is illustrated in general flowchart format the various steps taken by the system 10 in order to automatically visually inspect an article such as the circuit 12. After an image is acquired by the illumination and imaging subsystem 14, the fixture 13 is moved under control of the system 26 along line 50. Prior to detecting flaws in the acquired image, the image data is then segmented by a segmentation algorithm to identify the materials i.e. conductor, resistor, dielectric, solder, etc. from the gray scale data produced by the imaging subsystem 14. Most vision algorithms require some type of segmentation to separate the objects of interest from the background. The segmentation algorithm is shown in greater detail in FIG. 6. Briefly, the segmentation procedure reduces the range of gray values into several distinct states, each of which represents a particular pattern, class or material within the image.

Figure 6:
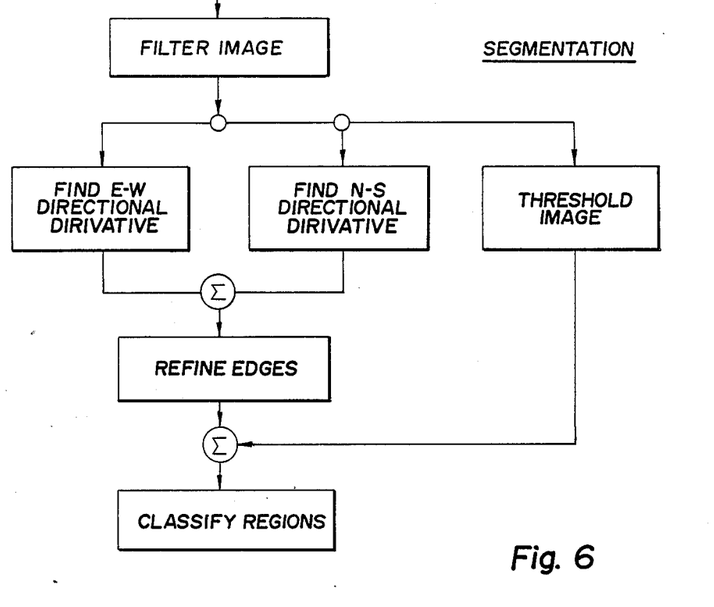
FIG. 6 is a more detailed block diagram of the segmentation algorithm of the present invention.

Segmentation by thresholding is a simple fast technique which is useful if high dimensional accuracy is not required and if a high contrast, very stable input image is available. However, if dimensional accuracy and stability are required for gauging, as in the case of identifying the various layers of a thick film circuit, then a segmentation algorithm which uses both intensity levels (i.e. thresholding) and spatial information (i.e. edge information) as shown in FIG. 6 is required. In FIG. 6, the original image is first filtered by non-linear or "order statistic" filters which smooth between boundaries in the image but do not blur edges. Thresholding of the image is then performed by a histogram analysis routine to help identify homogeneous regions. East, west, south and north directional derivatives are thereafter applied to the filtered data in order to get good image edges for gauging. This is accomplished by applying such functions as a Sobel operator and maximum neighbor selection functions to the filtered data in the pipeline 28.

Thereafter, the directional derivatives are combined and the edges are refined such as by edge linking, edge classification, recruitment, weak edge suppression, closing small gaps and edge thinning.

Finally, the spatial information is applied to the threshold image to resolve ambiguities by classifying pixels in the border regions based upon their relationship to the neighboring homogeneous regions, thus providing accurate locations of each of the patterns or regions.

Figure 8:
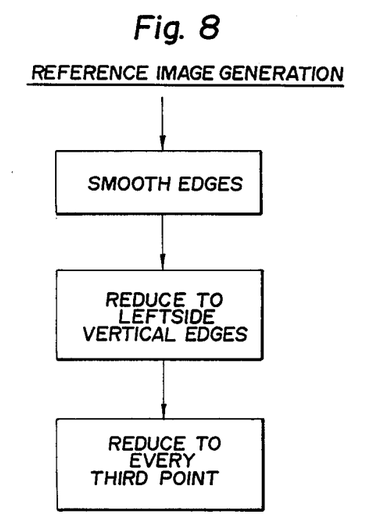
FIG. 8 is a more detailed block diagram of the reference image generation algorithm of the present invention.

Referring again to FIG. 5, after segmentation an image-like representation (i.e. a topology map) of a good known circuit must be constructed in order to use the reference or pattern matching method of defect detection. In order to avoid excessive memory costs and slow data transfer rates, the reference image is compacted or compressed as shown in FIG. 8 to reduce the number of data points which represents the reference image prior to storing same. Initially, the edges between adjacent areas in the data are smoothed. Then the data is reduced to a left-sided, vertical edge. Thereafter, the vertical edges are reduced so that only every third pixel is represented. Finally, the remaining points are stored.

Figure 9:
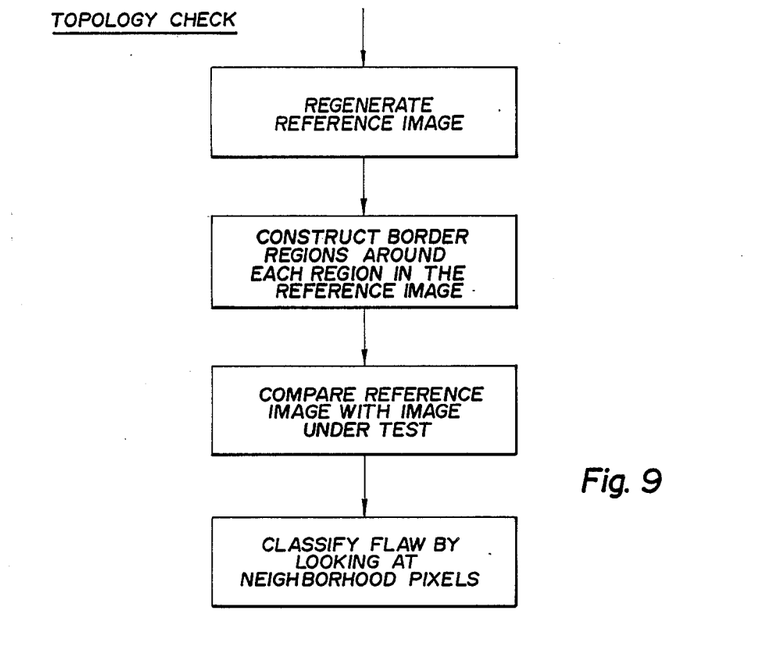
FIG. 9 is a more detailed block diagram of the topology check algorithm of the present invention.

In order to check the topology of a circuit under test, the reference image is regenerated by reversing the data compression algorithm in the pipeline 28 as shown in FIG. 9. Border regions are constructed around each region in the reference image. Then a direct comparison is made between the reference image and the image under test to locate any flaws and determine the defect type. A thinning operator is applied to both inside and outside the area of overlap to check for continuity in order to classify the flaws. This technique does not require processing of the image under test, but only processing of the reference image. This method provides a direct method for determining location, size and context information for the detected flaw. Mismatches between the image under test and the reference image are characterized as flaws. The extent of the flaw is determined by expanding the defective region over the flawed region to preserve the size, type and location of the flaw.

Figure 7:
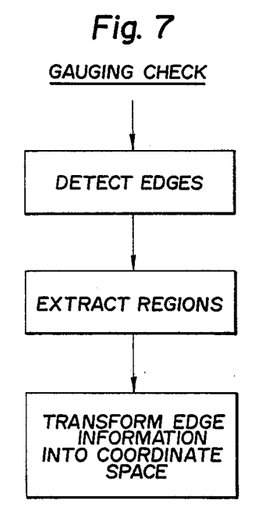
FIG. 7 is a more detailed block diagram of the gauging check algorithm of the present invention.

Referring again to FIG. 5 and to FIG. 7, a gauging check algorithm is provided for dimensional measurement. The algorithm provides sub-pixel accuracy despite digitization noise. Initially, an edge detection step is used to obtain an edge location representation of the circuit under test. Then the coordinates of the connected edge components are extracted from the image. Finally, lines or curves are fitted to the coordinates of the connected edge components in a least squares gauging module to locate the line and curve segments with high precision. In this way, the edge can be located within an accuracy of at least plus or minus 0.5 pixels.

Figure 10:
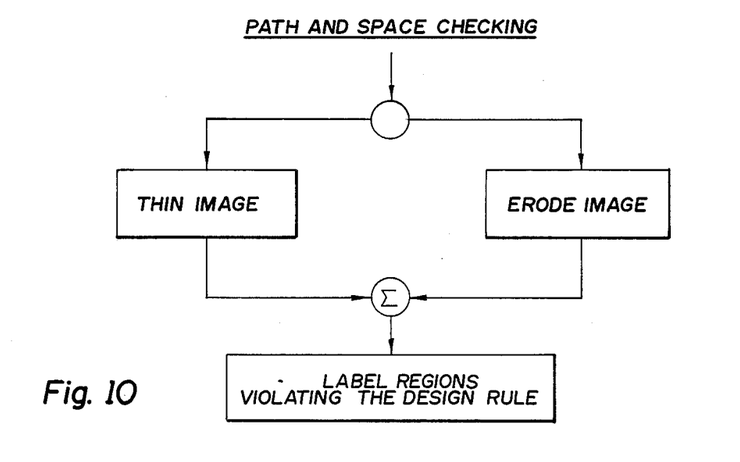
FIG. 10 is a more detailed block diagram of the path and space checking algorithm of the present invention.

Referring again to FIG. 5 and to FIG. 10 there is illustrated a path and space checking algorithm which supplements the reference method of FIG. 9. In general, the path and space algorithm checks patterns which "neck down" or have other irregularities, such as small, concave regions.

Initially, the image is thinned to locate circuit paths. Then, the input image is eroded or contracted to label areas which violate a minimum design rule. Finally, the results of the first two steps are combined to label all paths where a violation occurred. Any path which is below the design rule will be flagged. Defects larger than the design rule are detected by the topology check method.

By utilizing both the reference and non-reference algorithms, flaw coverage overlaps. For example, some of the flaws illustrated in FIG. 3 will be detected by both methods. Another advantage is that the system 10 can be programmed to execute very efficiently, leading to a high throughput system when both reference and nonreference methods are utilized. Furthermore, because the complexity of multilayer hybrid circuits is steadily increasing, the invariant sets of rules of the non-reference method sufficient for detection of all defects is increasingly difficult to specify. Even if such rules could be specified, they would be very long, resulting in a time-consuming algorithm.

The advantages of the above-described system and method are numerous. For example, the system 10 is designed for high throughput and high accuracy while remaining a cost-effective solution to practical circuit inspection problems. This is accomplished by combining reference, non-reference and measurement methods or algorithms in a system which is general and also applicable to the inspection of other types of circuits such as PWB's and IC's. Such a method and system is also capable of inspecting two-dimensional patterns having several colors and shades of gray. Such applications also include character recognition, inspecting for defects in disks and tapes, CRT inspection, etc.

While the best mode for carrying out the invention has been described herein in detail, those skilled in the art to which this invention relates will recognize various alternative designs and embodiments for practicing the invention as defined by the following claims.

What is claimed is:

1. A method for automatically and visually inspecting an article, the method comprising the steps of:
    acquiring a first set of digital image data representing a known good article, the image data representing a two dimensional reference image, processing the first set of image data to separate the reference image into at least two identifiable areas having a boundary therebetween;
    compressing the reference image in each of the two dimensions of the reference image, the step of compressing including the steps of reducing at least one of the areas of the reference image to an edge represented by a number of data points and reducing the number of data points representing the edge;
    storing the compressed reference image;
    acquiring a second set of digital image data representing a two-dimensional image of an article under inspection;
    processing the second set of digital image data to separate the image of the article under inspection into at least two identifiable areas having a boundary therebetween;

retrieving the compressed reference image;

regenerating the retrieved reference image, said step of regenerating including the step of regenerating the edge from the reduced number of data points, regenerating the at least one of the areas from the regenerated edge, and constructing border regions around at least one of the areas of the reference image to obtain a regenerated reference image; and matching the regenerated reference image and the image of the article under inspection to identify areas where mismatches occur.

2. The method as claimed in claim 1 wherein the article includes electronic circuitry such as a multilayer thick-film circuit having a plurality of components.

3. The method as claimed in claim 1 or 2 including the step of measuring at least one dimension of one of the areas of the image of the article under inspection.

4. The method as claimed in claim 1 or 2 further comprising the step of checking the second set of processed data with at least one preselected geometrical constraint to identify areas of non-compliance.

5. The method as claimed in claim 4 wherein the step of checking includes the step of checking the second set of image data with a preselected width constraint.

6. The method as claimed in claim 4 wherein the step of checking includes the step of performing a series of neighborhood transformations on said second set of image data.

7. The method as claimed in claim 6 including the step of generating a bit map flagging the areas of non-compliance.

8. The method as claimed in claim 4 including the step of combining said areas of non-compliance and said areas where the mismatches occur to identify defects.

9. A system for automatically, visually inspecting an article, the system comprising:

means for acquiring first and second sets of digital image data, the first set of image data representing a two-dimensional reference image of a known good article and the second set of image data representing a two-dimensional image of the article under inspection;

means for processing the first set of image data to separate the first set of image data into at least two identifiable areas having a boundary therebetween;

means for compressing the reference image in each of the two dimensions of the reference image, said means for compressing including means for reducing at least one of the areas of the reference image to an edge represented by a number of data points and means for reducing the number of data points representing the edge;

means for storing the compressed reference image;

means for retrieving the stored compressed reference image;

means for regenerating the reference image, said means for regenerating including means for regenerating the edge from the reduced number of data points representing the edge, means for regenerating the at least one of the areas of the reference image from the edge; and means for constructing border regions from the at least one of the areas of the reference image to obtain the regenerated reference image; and means for matching the regenerated reference image and the image of the article under inspection to identify areas where mismatches occur.

10. The system as claimed in claim 9 wherein the article includes circuitry such as a multilayer thick film circuit having a plurality of components.

11. The system as claimed in claim 9 wherein said means for matching includes an arithmetic logic unit for comparing the regenerated reference image and the second set of processed image data.

12. The system as claimed in claim 10 further comprising means for checking the set of processed image data with at least one preselected geometrical constraint to identify areas of non-compliance.

13. The system as claimed in claim 12 wherein said means for checking includes a pipeline of serial neighborhood transformation stages for processing the second set of image data.

14. The system as claimed in claim 13 wherein said means for matching includes an arithmetic logic unit selectively coupled to the output of the pipeline and selectively coupled to said means for regenerating for combining the regenerated reference image and the second set of image process data.

* * * * *